(12) United States Patent
Hillukka et al.

(10) Patent No.: US 11,517,714 B2
(45) Date of Patent: Dec. 6, 2022

(54) MEDICAL DEVICE INCLUDING AN ACTUATOR RESTRAINING ASSEMBLY

(71) Applicant: St. Jude Medical, Cardiology Division, Inc., St. Paul, MN (US)

(72) Inventors: Brett A. Hillukka, Hanover, MN (US); Evan M. Leingang, Plymouth, MN (US); Richard A. Thompson, II, St. Louis Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 435 days.

(21) Appl. No.: 16/869,029

(22) Filed: May 7, 2020

(65) Prior Publication Data

US 2020/0261697 A1    Aug. 20, 2020

Related U.S. Application Data

(62) Division of application No. 15/450,496, filed on Mar. 6, 2017, now Pat. No. 10,675,443.

(Continued)

(51) Int. Cl.
*A61M 25/01* (2006.01)

(52) U.S. Cl.
CPC .... *A61M 25/0136* (2013.01); *A61M 25/0113* (2013.01); *A61M 25/0147* (2013.01)

(58) Field of Classification Search
CPC .......... A61M 25/0105; A61M 25/0136; A61M 25/0147; A61B 2017/003; A61B 2017/0038; A61B 2017/00367
See application file for complete search history.

(56) References Cited

U.S. PATENT DOCUMENTS

| 4,139,222 A | 2/1979 | Loland |
| 4,196,730 A | 4/1980 | Wilson |

(Continued)

FOREIGN PATENT DOCUMENTS

| EP | 0839547 A1 | 5/1998 |
| EP | 1205208 A1 | 5/2002 |

(Continued)

OTHER PUBLICATIONS

Machine Translation of Matsuda WO 2011/142142 A1 (Year: 2011).*

(Continued)

*Primary Examiner* — Laura A Bouchelle
(74) *Attorney, Agent, or Firm* — Armstrong Teasdale LLP (57) ABSTRACT

The present disclosure provides a medical device comprising an actuator restraining assembly configured to assist in restraining a catheter shaft in a deflected configuration. The actuator restraining assembly may include a brake element, a release element, a connecting sheath, and a connecting rod disposed in a catheter handle, wherein the connecting sheath and connecting rod are attached to an actuator mechanism, and wherein the at brake element is attached to the connecting sheath and the release element is attached to the connecting rod. The brake element is sized and configured to contact an inner wall of the handle to thereby provide resistance to movement of actuator mechanism in a proximal direction with respect to the handle. In one embodiment, the actuator restraining assembly is configured to allow for temporary, i.e., reversible, restraining of the catheter shaft in the deflected configuration.

9 Claims, 5 Drawing Sheets

Related U.S. Application Data (60) Provisional application No. 62/304,386, filed on Mar. 7, 2016.

(56) References Cited

U.S. PATENT DOCUMENTS

| | | |
|---|---|---|
| 4,203,430 A | 5/1980 | Takahashi |
| 4,960,134 A | 10/1990 | Webster, Jr. |
| 5,104,274 A | 4/1992 | Omori |
| 5,125,895 A | 6/1992 | Buchbinder et al. |
| 5,125,896 A | 6/1992 | Hojeibane |
| 5,269,115 A | 12/1993 | Stentenbach |
| 5,269,757 A | 12/1993 | Fagan et al. |
| RE34,502 E | 1/1994 | Webster, Jr. |
| 5,277,199 A | 1/1994 | DuBois et al. |
| 5,281,217 A | 1/1994 | Edwards et al. |
| 5,318,525 A | 6/1994 | West et al. |
| 5,327,889 A | 7/1994 | Imran |
| 5,327,905 A | 7/1994 | Avitall |
| 5,327,906 A | 7/1994 | Fideler et al. |
| 5,330,466 A | 7/1994 | Imran |
| 5,342,295 A | 8/1994 | Imran |
| 5,354,297 A | 10/1994 | Avitall |
| 5,364,351 A | 11/1994 | Heinzelman et al. |
| 5,383,923 A | 1/1995 | Webster, Jr. |
| 5,389,073 A | 2/1995 | Imran |
| 5,391,147 A | 2/1995 | Imran et al. |
| 5,395,328 A | 3/1995 | Ockuly et al. |
| 5,395,329 A | 3/1995 | Fleischhacker et al. |
| 5,397,304 A | 3/1995 | Truckai |
| 5,431,168 A | 7/1995 | Webster, Jr. |
| 5,441,483 A | 8/1995 | Avitall |
| 5,445,148 A | 8/1995 | Jaraczewski et al. |
| 5,478,330 A | 12/1995 | Imran et al. |
| 5,487,385 A | 1/1996 | Avitall |
| 5,487,757 A | 1/1996 | Truckai et al. |
| 5,527,279 A | 6/1996 | Imran |
| 5,531,687 A | 7/1996 | Snoke |
| 5,533,967 A | 7/1996 | Imran |
| 5,545,200 A | 8/1996 | West |
| 5,562,619 A | 10/1996 | Mirarchi et al. |
| 5,582,609 A | 12/1996 | Swanson et al. |
| 5,588,964 A | 12/1996 | Imran et al. |
| 5,611,777 A | 3/1997 | Bowden et al. |
| 5,626,136 A | 5/1997 | Webster, Jr. |
| 5,656,029 A | 8/1997 | Imran et al. |
| 5,656,030 A | 8/1997 | Hunjan et al. |
| 5,741,320 A * | 4/1998 | Thornton .......... A61M 25/0147 604/95.01 |
| 5,755,760 A | 5/1998 | Maguire et al. |
| 5,779,669 A | 7/1998 | Hassaguerre et al. |
| 5,807,249 A | 9/1998 | Qin et al. |
| 5,826,576 A | 10/1998 | West |
| 5,827,272 A | 10/1998 | Breining et al. |
| 5,827,278 A | 10/1998 | Webster |
| 5,836,947 A | 11/1998 | Fleischman et al. |
| 5,842,984 A | 12/1998 | Avitall |
| 5,843,031 A | 12/1998 | Hermann et al. |
| 5,843,076 A | 12/1998 | Webster, Jr. et al. |
| 5,861,024 A | 1/1999 | Rashidi |
| 5,865,800 A | 2/1999 | Mirachi et al. |
| 5,885,278 A | 3/1999 | Fleischman et al. |
| 5,897,529 A | 4/1999 | Ponzi |
| 5,910,129 A | 6/1999 | Koblish et al. |
| 5,916,213 A | 6/1999 | Haissaguerre et al. |
| 5,916,214 A | 6/1999 | Cosio et al. |
| 5,921,924 A | 7/1999 | Avitall |
| 5,931,811 A | 8/1999 | Hasissaguerre et al. |
| 5,935,102 A | 8/1999 | Bowden et al. |
| 5,944,690 A | 8/1999 | Falwell |
| 5,987,344 A | 11/1999 | West |
| 5,993,462 A | 11/1999 | Pomeranz et al. |
| 6,002,955 A | 12/1999 | Willems et al. |
| 6,024,722 A | 2/2000 | Rau et al. |
| 6,027,473 A | 2/2000 | Ponzi |
| 6,033,403 A | 3/2000 | Tu et al. |
| 6,048,329 A | 4/2000 | Thompson et al. |
| 6,059,739 A | 5/2000 | Baumann |
| 6,064,902 A | 5/2000 | Haissaguerre et al. |
| 6,066,125 A | 5/2000 | Webster, Jr. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,083,222 A | 7/2000 | Klein et al. |
| 6,090,104 A | 7/2000 | Webster, Jr. |
| 6,123,699 A | 9/2000 | Webster, Jr. |
| 6,138,043 A | 10/2000 | Avitall |
| 6,149,663 A | 11/2000 | Stranberg et al. |
| 6,169,916 B1 | 1/2001 | West |
| 6,171,277 B1 | 1/2001 | Ponzi |
| 6,178,354 B1 | 1/2001 | Gibson |
| 6,183,435 B1 | 2/2001 | Baunbalough et al. |
| 6,183,463 B1 | 2/2001 | Webster, Jr. |
| 6,198,974 B1 | 3/2001 | Webster, Jr. |
| 6,200,315 B1 | 3/2001 | Gaiser et al. |
| 6,203,507 B1 | 3/2001 | Wadsworth et al. |
| 6,203,525 B1 | 3/2001 | Whayne et al. |
| 6,210,362 B1 | 4/2001 | Ponzi |
| 6,210,407 B1 | 4/2001 | Webster |
| 6,214,002 B1 | 4/2001 | Fleischman et al. |
| 6,221,087 B1 | 4/2001 | Anderson et al. |
| 6,224,587 B1 | 5/2001 | Gibson |
| 6,241,754 B1 | 6/2001 | Swanson et al. |
| 6,308,091 B1 | 10/2001 | Avitall |
| 6,332,633 B1 | 12/2001 | Fitoussi et al. |
| 6,375,654 B1 | 4/2002 | McIntyre |
| 6,430,426 B2 | 8/2002 | Avitall |
| 6,454,758 B1 | 9/2002 | Thompson et al. |
| 6,456,034 B1 | 9/2002 | Vilou |
| 6,464,645 B1 | 10/2002 | Park et al. |
| 6,533,783 B1 | 3/2003 | Tollner |
| 6,582,536 B2 | 6/2003 | Shimda |
| 6,652,506 B2 | 11/2003 | Bowe |
| 6,728,563 B2 | 4/2004 | Rashidi |
| 6,743,227 B2 | 6/2004 | Seraj et al. |
| 7,819,297 B2 | 10/2010 | Doll et al. |
| 7,892,215 B2 | 2/2011 | Melsheimer et al. |
| 8,167,660 B2 | 5/2012 | Dilmaghanian et al. |
| 8,328,767 B2 | 12/2012 | Solomon et al. |
| 8,366,635 B2 | 2/2013 | Parihar et al. |
| 2002/0032365 A1 | 3/2002 | Hasegawa |
| 2002/0082584 A1 | 6/2002 | Rosenman et al. |
| 2003/0149422 A1 | 8/2003 | Muller |
| 2005/0038333 A1 | 2/2005 | Sra |
| 2006/0142695 A1 | 6/2006 | Knudson |
| 2008/0009928 A1 | 1/2008 | Osypka et al. |
| 2010/0160858 A1 | 6/2010 | Fischer et al. |
| 2011/0264074 A1 | 10/2011 | Tegg et al. |
| 2011/0282176 A1 | 11/2011 | Tegg |

FOREIGN PATENT DOCUMENTS

| | | |
|---|---|---|
| EP | 1905376 A2 | 4/2008 |
| GB | 1170018 A | 11/1969 |
| JP | H05-033736 U | 5/1993 |
| JP | H5229730 | 9/1993 |
| JP | H11-000373 | 1/1999 |
| JP | 3068688 U | 5/2000 |
| JP | 2001178828 A | 7/2001 |
| JP | 2001275928 A | 10/2001 |
| JP | 2007524439 A | 8/2007 |
| JP | 2011234977 A | 11/2011 |
| WO | 9304724 A1 | 3/1993 |
| WO | 1994001162 A2 | 1/1994 |
| WO | 1994004220 A1 | 3/1994 |
| WO | 9943377 A1 | 9/1999 |
| WO | 2004087249 A2 | 10/2004 |
| WO | 2007002713 A2 | 1/2007 |
| WO | 2007136984 A2 | 11/2007 |

(56) References Cited

FOREIGN PATENT DOCUMENTS

WO        2011142142 A1    11/2011
WO    WO-2011142142 A1 *   11/2011          A61M 25/0136

OTHER PUBLICATIONS

Supplementary European Search Report, EP 07761909, dated Apr. 12, 2011.
International Search Report for PCT Application No. PCT/US06/25082, dated Sep. 12, 2007. 3 pgs.
International Search Report for PCT Application No. PCT/US2007/068269, dated Dec. 3, 2008. 3 pgs.
International Search Report and Written Opinion for PCT Application No. PCT/US2014/015247, dated Jun. 17, 2014, 13 pgs.
International Search Report for PCT Application No. PCT/US2014/070762, dated Mar. 20, 2015, 4 pgs.
Standard Handbook of Machine Design, ref. p. 6.40 Section 6.7 (Table 6.15), 10 pags, Digital Engineering Library, www.digitalengineeringlibrary.com, 2004.

* cited by examiner

MEDICAL DEVICE INCLUDING AN ACTUATOR RESTRAINING ASSEMBLY

A. CROSS-REFERENCE TO RELATED APPLICATION

This application is a divisional of U.S. Non-Provisional patent application Ser. No. 15/450,496, filed Mar. 6, 2017, entitled "MEDICAL DEVICE INCLUDING AN ACTUATOR RESTRAINING ASSEMBLY", which claims the benefit of priority to U.S. Provisional Patent Application No. 62/304,386, filed Mar. 7, 2016, entitled "MEDICAL DEVICE INCLUDING AN ACTUATOR RESTRAINING ASSEMBLY," the entire contents of which are hereby incorporated by reference in their entirety.

B. FIELD OF DISCLOSURE

The present disclosure relates generally to medical devices that are used in the human body. In particular, in many embodiments, the present disclosure relates to a medical device actuator restraining assembly for assisting in holding, retaining, and/or locking a medical device actuator mechanism in a desired position during use while allowing the release of the medical device actuator mechanism to another position as desired. The present disclosure may be particularly useful in plunger-type uni-directional catheter handles.

C. BACKGROUND

Medical devices, such as catheter systems, are well known in the art for use in medical procedures, such as diagnostic (e.g., cardiac mapping) and therapeutic procedures (e.g., cardiac ablation). Typical catheter systems generally include an elongated flexible catheter shaft extending from a control handle containing an actuating mechanism. A physician manipulates the catheter shaft through the patient's vasculature to an intended site within the patient via the actuating mechanism contained within the control handle.

An actuating mechanism of the catheter system may include mechanical steering features or components that may be manually manipulated to position a catheter shaft within the body at a desired site or to operate the catheter system during use. In some embodiments, a catheter or catheter system may be positioned within a patient's vasculature during a procedure by simultaneous application of torque or force at the proximal end of the catheter and/or by selectively deflecting the distal tip of the catheter in a desired direction.

The distal tip of the catheter can be deflected by a pull wire or other tension member attached or anchored at the distal end of the catheter and extending proximally to an actuator mechanism in a control handle that controls the application of tension on the pull wire. Distal movement of the catheter shaft with respect to a body of the control handle, upon the application of an external force on the actuating mechanism, may impose eccentric pull forces on the distal portion of the catheter shaft resulting in the distal portion of the catheter shaft assuming a deflected configuration. Absent an external force exerted on the actuating mechanism, the catheter shaft tends to return to its natural, unstressed neutral position due to the force exerted on it by the strained pull wire.

BRIEF SUMMARY OF THE DISCLOSURE

The present disclosure provides a means of holding or "locking" an actuating mechanism (such as a handle plunger) on a medical device in a deflected state without the need for a secondary restraining or "locking" mechanism within the medical device. The present disclosure may be particularly useful with uni-directional catheter handles that include a split actuator mechanism. The present disclosure also provides a means to reduce the plunger force experienced by a user during the deflection of a medical device such that use fatigue is lessened or eliminated. Various embodiments of the present disclosure are set forth herein.

In one embodiment, the present disclosure is directed to an actuator restraining assembly for a medical device comprising a handle, a connecting sheath disposed in the handle and coupled to a proximal actuator mechanism, a connecting rod disposed at least partially in the connecting sheath and coupled to a distal actuator mechanism, at least one brake element attached to the connecting sheath, and at least one release element coupled to the at least one brake element and attached to the connecting rod. The at least one brake element is sized and configured to contact an inner wall of the handle to thereby provide resistance to proximal movement of the connecting sheath with respect to the handle.

In another embodiment, the present disclosure is directed to a medical device comprising: (i) a catheter shaft having a proximal region and a deflectable distal region; (ii) an active drive assembly comprising a split actuator mechanism including a distal actuator mechanism and a proximal actuator mechanism, wherein the split actuator mechanism is configured to engage the proximal region of the catheter shaft and is at least partially movable with respect to a handle along a longitudinal axis thereof; and (iii) an actuator restraining assembly comprising a connecting sheath, a connecting rod, a brake element and a release element, disposed in the handle. The connecting rod is disposed at least partially in the connecting sheath and is attached to the distal actuator mechanism and the connecting sheath is attached to the proximal actuator mechanism. The brake element is attached to the connecting sheath, the release element is coupled to the brake element and attached to the connecting rod, and the brake element is sized and configured to contact an inner wall of the handle to thereby provide resistance to proximal movement of the connecting sheath with respect to the handle.

In another embodiment, the present disclosure is directed to a method of deflecting a distal region of a medical device. The method comprises (i) providing a medical device comprising: (a) a catheter shaft having a proximal region and a deflectable distal region; (b) an active drive assembly comprising a distal actuator mechanism and a proximal actuator mechanism, wherein the distal and proximal actuator mechanisms are configured to engage the proximal region of the catheter shaft and are at least partially movable with respect to a handle along a longitudinal axis thereof; and (c) an actuator restraining assembly comprising a connecting sheath, a connecting rod, a brake element, and a release element, disposed in the handle, wherein the connecting rod is disposed at least partially in the connecting sheath and is attached to the distal actuator mechanism and the connecting sheath is attached to the proximal actuator mechanism, and wherein the brake element is attached to the connecting sheath, the release element is coupled to the brake element and attached to the connecting rod, and the brake element is sized and configured to contact an inner wall of the handle to thereby provide resistance to proximal movement of the connecting sheath with respect to the handle; (ii) distally advancing the proximal actuator mechanism with respect to the handle to a position wherein the deflectable distal region of the catheter shaft is in a deflected configuration; and (iii)

allowing the proximal actuator mechanism to at least partially retract in a proximal direction with respect to the handle such that at least a portion of an inner surface of handle is contacted by the brake element to create a frictional resistance therebetween sufficient to limit further proximal movement of the proximal actuator mechanism with respect to the handle.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure provides medical devices including catheter systems suitable for use in the human vasculature for known medical procedures. Catheter systems of the multiple embodiments of the present disclosure exhibit a "self-locking" feature upon the catheter system being positioned in a deflected configuration; that is, the present disclosure provides embodiments wherein an actuator mechanism of a catheter system is restrained or locked in the position in which a distal region of the catheter system, such as the distal region of a catheter shaft, is in a deflected configuration, without the need for a user to perform an additional "locking" step to maintain the actuator mechanism in the desired position. Because the "automatic" or "self-locking" feature does not permanently fix the actuator mechanism in a particular position, the "self-locking" features disclosed herein are also reversible upon the application of a sufficient external force on the actuator mechanism in either the proximal direction (to reduce the amount of deflection of the catheter shaft) or the distal direction (to increase the amount of deflection of the catheter shaft). Such disclosed embodiments may lead to more consistent and improved patient outcomes, as well as a reduced amount of fatigue for the user. For purposes of this description, the present disclosure will be described in connection with numerous embodiments of a uni-directional plunger-type catheter including an actuator restraining assembly as described herein. It is contemplated, however, that the described features and methods of the present disclosure as described herein may be incorporated into any number of catheters or other medical devices as would be appreciated by one of ordinary skill in the art based on the disclosure herein.

More specifically, some embodiments of the present disclosure provide a catheter system including an actuator restraining assembly comprising a brake element, a release element, a connecting sheath, and a connecting rod all disposed in a catheter handle that is connected to a deflectable member, such as a deflectable catheter shaft. The connecting rod is at least partially disposed in the connecting sheath. The connecting sheath is attached to an actuator mechanism and to the brake element and the connecting rod is attached to an actuator mechanism and the release element. The brake element is sized and configured to contact an inner wall of the handle upon proximal movement of the connecting sheath (with respect to the handle) to thereby provide resistance to movement of the connecting sheath (and hence the actuator mechanism) in a proximal direction with respect to the handle. This provides a "locking mechanism" to the connecting sheath, and hence to the actuator mechanism, which may, in many embodiments, lead to an increased life cycle for the catheter device and a reduced plunger force experienced by the user during deflection as described herein. Other embodiments described herein include methods of using the catheter system including the actuator restraining assembly.

The actuator restraining assembly as described herein provides a mechanistic way by which an actuator mechanism may be restrained, or "locked," in a particular position during use of a deflectable catheter system without the need for performing an additional locking step. That is, catheter systems including a deflectable catheter shaft known in the art oftentimes utilize an eccentric pull wire configured to interact with an actuator mechanism via a catheter shaft in order to initiate the defection of the distal region of the catheter shaft. As discussed in greater detail below, during use of catheter systems such as these, a user may advance an actuator mechanism (also referred to as an actuator lever) distally, thus causing a proximal end of the pull wire, which may be mounted or fastened to a gripper, to move along with the catheter shaft until such movement is stopped or prohibited by an obstacle (or shoulder) positioned within the handle housing. Continued distal movement of the catheter shaft, driven by the actuator mechanism, creates a high tension on the pull wire. Due to the eccentric fixation of the pull wire to the distal end of the catheter shaft, the tension on the pull wire generates the bending moment imposed on the distal region of the catheter shaft, leading to deflection of the distal region of the catheter shaft. At the same time, the tension on the pull wire leading to the deflection of the distal region results in the actuator mechanism tending to retract to a neutral (i.e., non-tensioned) state once a distal force is no longer imposed on the actuator mechanism. The various embodiments of the actuator restraining assembly described herein provide a frictional or mechanical resistance to limit undesired and/or unintentional retraction of the actuator mechanism (thus leading to the distal region of the catheter shaft reverting to a "neutral" or "un-deflected" configuration) without the need for a user to perform an additional "locking" step. Further, because the various embodiments of the restraining assembly disclosed herein do not permanently "fix" the actuator mechanism in the position corresponding to the deflected configuration of the catheter shaft, a user is able to proximally adjust the actuator mechanism during or after a procedure to provide the distal region of the catheter shaft with less or no deflection as compared to the original deflected configuration upon the application of an additional force; that is, the restraining of the actuator mechanism in the catheter deflected position is reversible.

Figure 1:
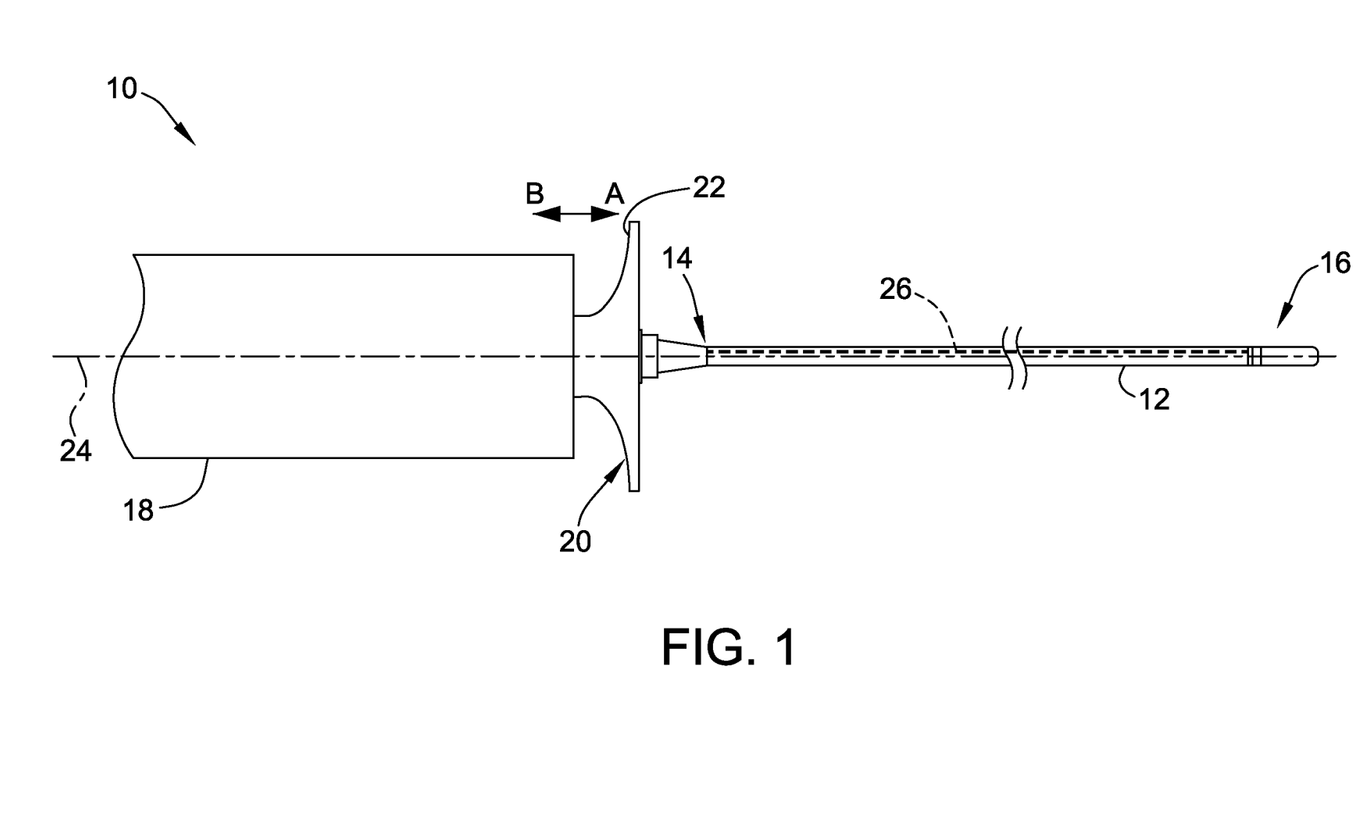
FIG. 1 is a perspective view of one embodiment of a catheter system including a handle, a catheter shaft, and an actuating mechanism.
Figure 2:
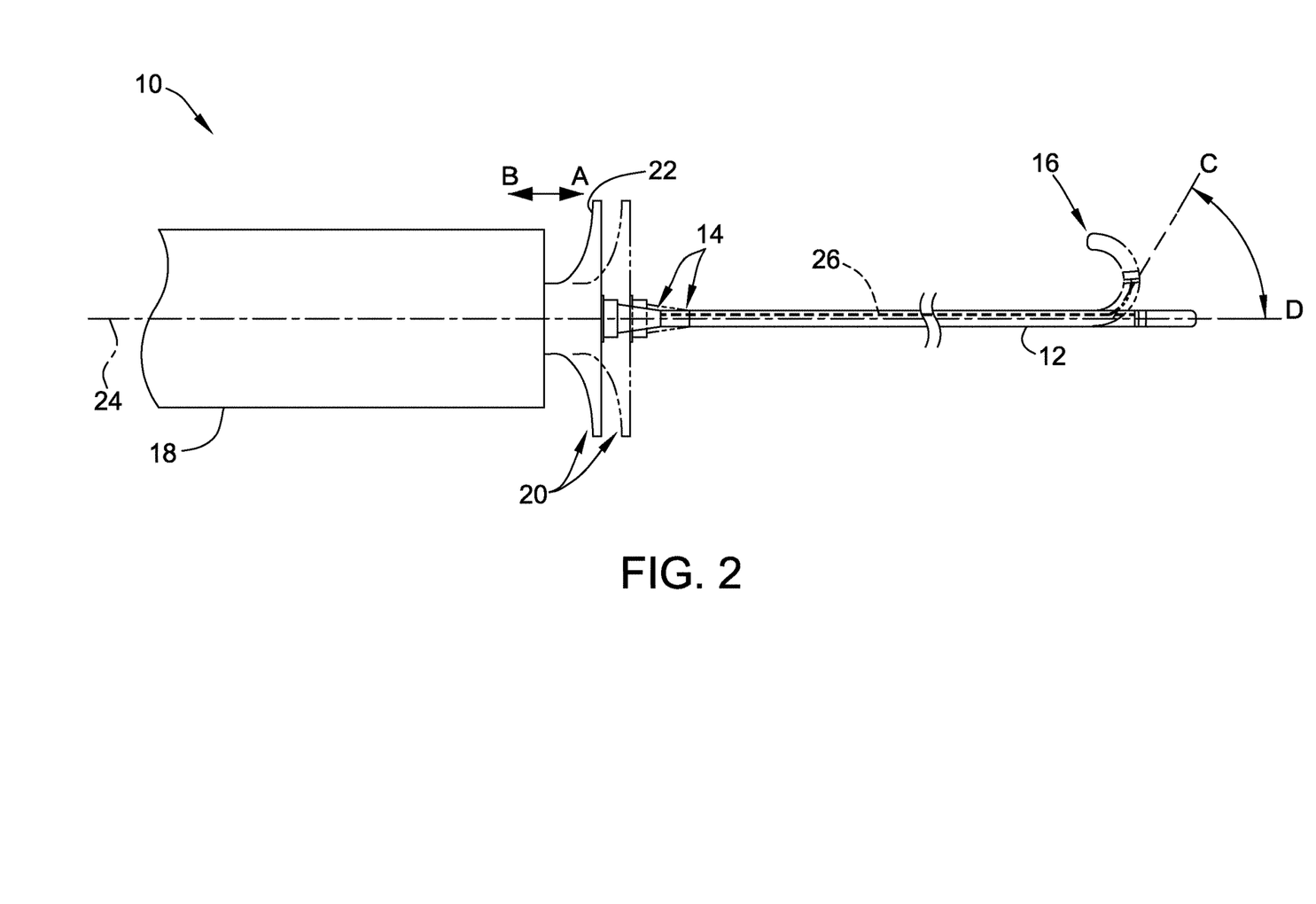
FIG. 2 illustrates the use of a pull wire to deflect the distal end of the catheter shaft of FIG. 1.

Referring now to the drawings, and specifically to FIG. 1, there is shown a plunger-type catheter 10 in an undeflected, or neutral position. Catheter 10 generally includes a catheter shaft 12, having a proximal region 14 and a deflectable distal region 16, a handle 18, pull wire 26, and an actuator housing (not shown). Handle 18 includes an actuator mechanism 20. As illustrated in FIGS. 1 and 2, actuator mechanism 20 includes an drive lever 22 (also commonly referred to as an "actuator lever" or "plunger") that is moveable relative to handle 18 along a central, longitudinal axis 24 of handle 18 in a first direction along arrow A (e.g., distally) that effects deflection of distal region 16 of catheter shaft 12 from the neutral position, as well as in a second, opposite direction along arrow B (e.g., proximally) that effects return or retraction of distal region 16 toward the neutral position. For example, catheter 10 can be of the type disclosed in United States Patent Application Publication No. 20150174369, filed Sep. 30, 2013 and published Jun. 25, 2015, which is hereby incorporated by reference as though fully set forth herein.

Referring now to FIG. 2 the use of pull wire 26 for deflecting distal region 16 of catheter shaft 12 is illustrated. Pull wire 26 extends through a lumen (not shown) of catheter shaft 12. Pull wire 26 is coupled to a pull ring (not shown) embedded in distal region 16 of catheter shaft 12 and to a gripper (not shown), such that movement of drive lever 22 in the first direction along arrow A effects deflection of distal region 16 of catheter shaft 12 from the neutral position along a first deflection direction (e.g., arrow C), and such that movement of drive lever 22 in the second direction along arrow B effects the return or retraction of distal region 16 of catheter shaft 12 towards the neutral position (e.g., along arrow D). Insofar as a person of ordinary skill in the art will appreciate the use of pull wires in a catheter, a detailed explanation of this aspect of the disclosure is not provided herein.

Figure 3A:
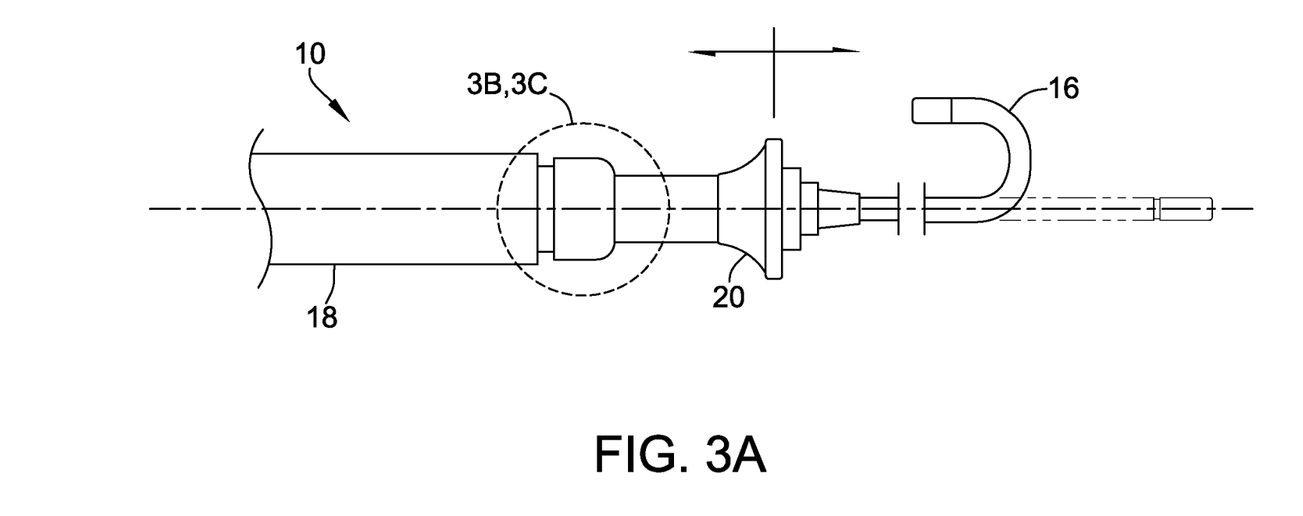
FIGS. 3A-3C illustrate an exemplary resilient friction assembly for use within the catheter handle of FIGS. 1 and 2.
Figure 3B:
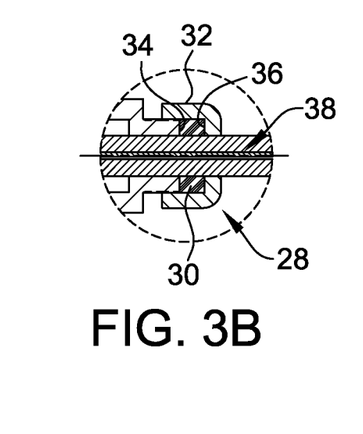
Figure 3C:
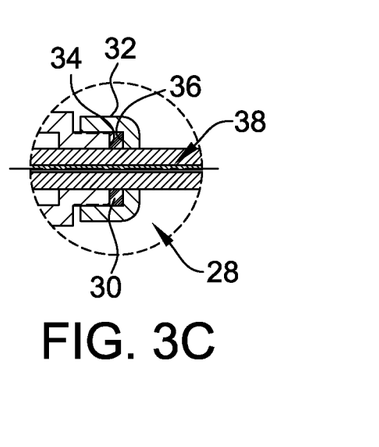

Now referring to FIGS. 3A-3C, there is further illustrated catheter 10 including handle 18, actuator mechanism 20, and deflectable distal region 16, with FIGS. 3B and 3C illustrating the internal construction of a portion thereof. Particularly, FIGS. 3B and 3C illustrate a resilient friction assembly 28 including resilient friction ring 30, such as a silicone ring, and locking mechanism 32, such as a threaded end cap or nut. Resilient friction ring 30 is positioned at a distal end 34 of handle 18 and proximal to locking mechanism 32 such that tightening of locking mechanism 32 (i.e., movement of locking mechanism 32 in a proximal direction with respect to handle 18) causes resilient friction ring 30 to be compressed between distal end 34 of handle 18 and a proximal surface of 36 of locking mechanism 32. Compression of resilient friction ring 30 thus causes an increase in friction between resilient friction ring 30 and a connecting rod 38 of actuator mechanism 20, which extends through resilient friction ring 30. This increased friction may therefore reduce the incidence of unintentional movement in a proximal or distal direction of connecting rod 38 with respect to handle 18, and provide a "locking feature."

Although the catheter systems disclosed herein are described primarily with respect to unidirectional catheters, it should be recognized that the disclosed principles are equally applicable in other contexts, including but not limited to, bidirectional catheters and other medical devices. That is, for example, with various structural arrangements of the restraining assembly discussed below, movement of drive lever 22 in the first direction along arrow A (See FIG. 2) could affect deflection of deflectable distal region 16 from the neutral position in a first defection direction (e.g., arrow C in FIG. 2), while movement of drive lever 22 in the second direction could affect deflection of deflectable distal region 16 from the neutral position in a second deflection direction, with both the first and second deflection directions lying in the same plane.

Plunger-type catheter 10 as illustrated in FIGS. 1, 2, and 3A-3C may further include an actuator restraining assembly configured to further restrain catheter shaft 12 in a position corresponding to a deflected configuration of deflectable distal region 16 without the need for an additional "locking" step being performed by a user (i.e., the restraining assembly is "self-locking"). That is, the restraining assembly is configured such that upon a user distally advancing drive lever 22 into a first position along arrow A (See FIG. 2) and thus deflecting deflectable distal region 16, the restraining assembly remains in the first position, thus holding deflectable distal region 16 in the desired deflected configuration upon a user no longer applying any force on drive lever 22. The restraining assembly is also configured to be releasable upon the application of a distal force (i.e., direction A in FIG. 2) or a proximal force (i.e., direction B in FIG. 2) on drive lever 22. As is described in more detail below, the restraining assembly exerts a frictional or mechanical force arising between components thereof and an inner wall of a handle. That is, the restraining assembly may provide a normal force and a frictional resistance against its impending movement with respect to a handle in a proximal direction (i.e., along arrow B) until a sufficient driving force is applied to drive lever 22 to overcome the frictional resistance exerted by the restraining assembly.

Figure 4:
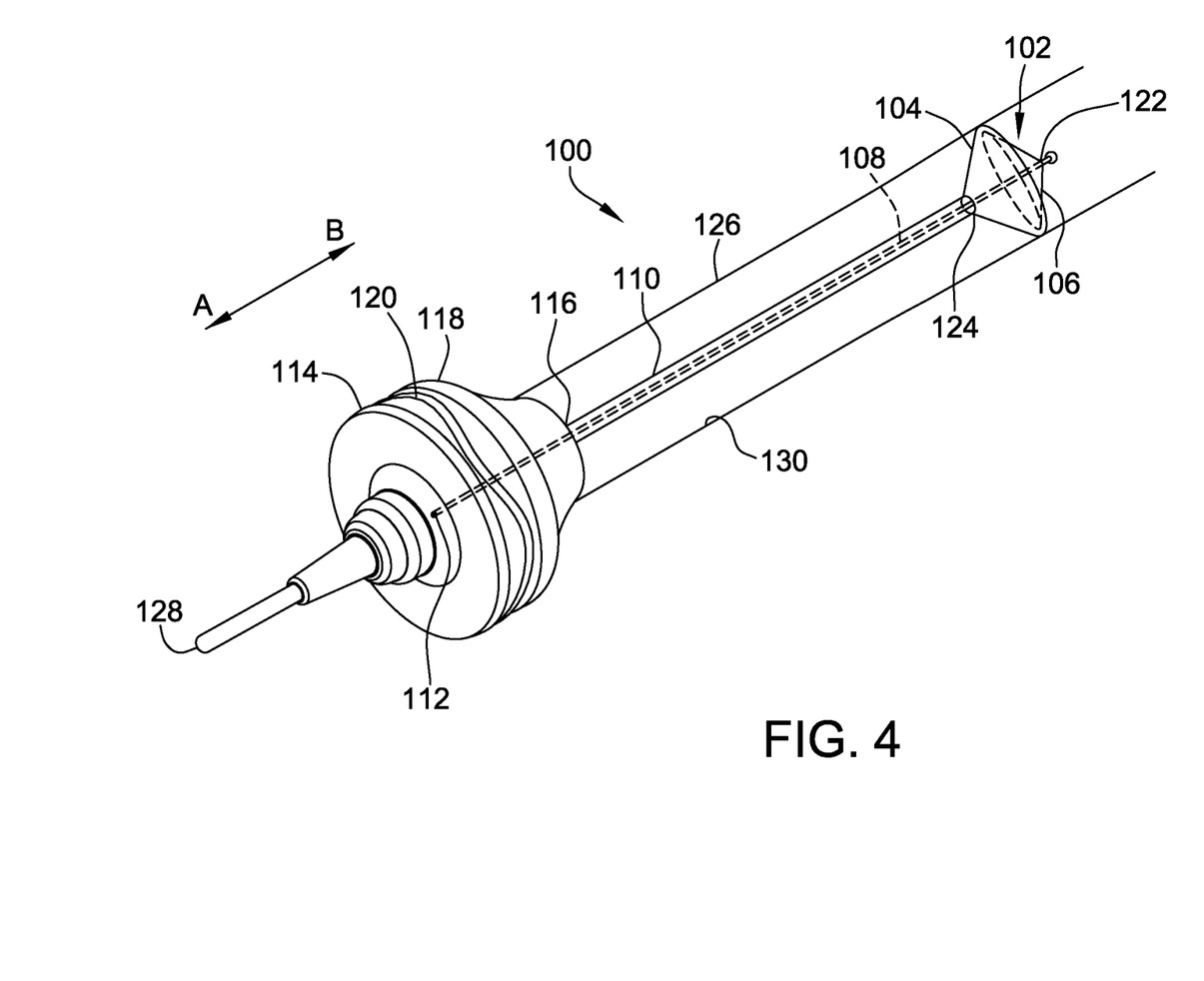
FIG. 4 is a cut-away view of a catheter including an exemplary actuator restraining assembly in accordance with multiple embodiments of the present disclosure.

Referring now to FIG. 4 and in accordance with the various embodiments of the present disclosure, there is illustrated a cut-away view of plunger-type catheter 100 including an exemplary actuator restraining assembly 102 and handle 126. Actuator restraining assembly 102 includes at least one brake element 104 coupled to at least one release element 106. Release element 106 is connected to connecting rod 108 at connection point 122 and brake element 104 is connected to connecting sheath 110 at connection point 124. A distal end 112 of connecting rod 108 is attached to a distal actuator mechanism 114 and a distal end 116 of connecting sheath 110 is attached to a proximal actuator mechanism 118. Distal actuator mechanism 114 and proximal actuator mechanism 118 are separated and held together by resilient member 120. Resilient member 120 (and resilient member 210 in FIGS. 5 and 6 described below) is generally illustrated herein as a single wave spring. However, it should be recognized that the resilient member could include multiple smaller springs arranged parallel to the longitudinal axis, a plurality of other springs, and/or a resilient or compressible material that allows the distal and proximal actuators to be compressibly connected.

In use, movement of proximal actuator mechanism 118 and distal actuator mechanism 114 in a direction along A as illustrated in FIG. 4 (or distally with respect to handle 126) causes movement of actuator restraining assembly 102 in the same direction, for example to deflect a catheter tip 128, while movement of distal actuator mechanism 114 and proximal actuator mechanism 118 in a direction along B as illustrated in FIG. 4 (or proximally with respect to handle 126) causes movement of actuator restraining assembly 102 in the same direction, for example to release deflection of catheter tip 128 to a neutral or un-deflected position. Specific use of actuator restraining assembly 102 is described in more detail below.

Brake element 104 and release element 106 may be attached to connecting sheath 110 and connecting rod 108, respectively, by any suitable means known in the art, so long as the connection point or points is stable and durable. As noted, the connection may be at a single point, or at multiple points, depending upon the exact design desired. In some embodiments, a ring element may be used for suitable connection. In other embodiments, attachment may be completed using such means as welding, soldering, bonding, joining, and/or adhering.

In some embodiments of the present disclosure, brake element 104 and release element 106 are both conical in shape, although other shapes/configurations of brake element 104 and release element 106, such as a stick or related configuration, are within the scope of the present disclosure. In some embodiments, conical shaping of brake element 104 may be desirable as this allows brake element 104 to contact an inner wall 130 of handle 126 as described in detail herein (and illustrated in FIG. 4) at multiple points about the circumference of inner wall 130 of handle 126 to provide improved braking or "locking." Generally, brake element 104 and release element 106 are the same shape, although it is within the scope of the present disclosure for brake element 104 and release element 106 to be different shapes.

Brake element 104 will generally have a longer length (as measured from a proximal end to a distal end along a surface thereof) as compared to release element 106 such that the "closing" (i.e., reducing the outer diameter of the proximal end of brake element 104) will also cause the "closing" of release element 106. Further, brake element 104 is generally sized and configured such that it is capable of contacting inner wall 130 of handle 126 to provide the braking or "locking" function upon movement of connecting sheath 110 in a proximal direction with respect to handle 126.

Brake element 104 and release element 106 as described herein may be constructed of any material of suitable strength and flexibility to carry out the desired function of each element as detailed herein. In one specific example, brake element 104 and release element 106 are constructed of a silicone based material.

In some embodiments of the present disclosure, brake element 104 and/or inner wall 130 of handle 126 (See FIG. 4) may include one or more friction increasing elements to improve the braking or "locking" performance of brake element 104 as further described herein. That is, brake element 104 and/or inner wall 130 of handle 126 may include an additional feature thereon to increase the friction, contact, engagement and/or grip between brake element 104 and inner wall 130 of handle 126 when they are contacted together upon movement in a particular direction (i.e., along line B in FIG. 4; see also along line D in FIGS. 5 and 6) in use as described herein to provide a "locking" benefit. The friction increasing element that may optionally be attached to brake element 104 and/or inner wall 130 of handle 126 may include teeth, grooves, ridges, slits, cuts, bumps, a high friction material, and combinations thereof. For example, in one exemplary embodiment, brake element 104 and inner wall 130 of handle 126 may include interfacing teeth to increase the braking or "locking" capability of brake element 104 when it contacts inner wall 130 of handle 126 as connecting sheath 110 moves along direction B as shown in FIG. 4. The interfacing teeth would be constructed for engagement and locking upon movement of brake element 104 in a specific direction, for example along line B in FIG. 4, but not along line A in FIG. 4. In another exemplary embodiment, inner wall 130 of handle 126 includes teeth and brake element 104 includes a high friction material thereon such that the teeth on inner wall 130 of handle 126 bite into the high friction material of brake element 104 as connecting sheath 110 moves along direction B as shown in FIG. 4. In another exemplary embodiment, inner wall 130 of handle 126 includes a high friction material and brake element 104 includes teeth such that the teeth on brake element 104 bite into the high friction material of inner wall 130 of handle 126 as connecting sheath 110 moves along direction B as shown in FIG. 4.

Figure 5:
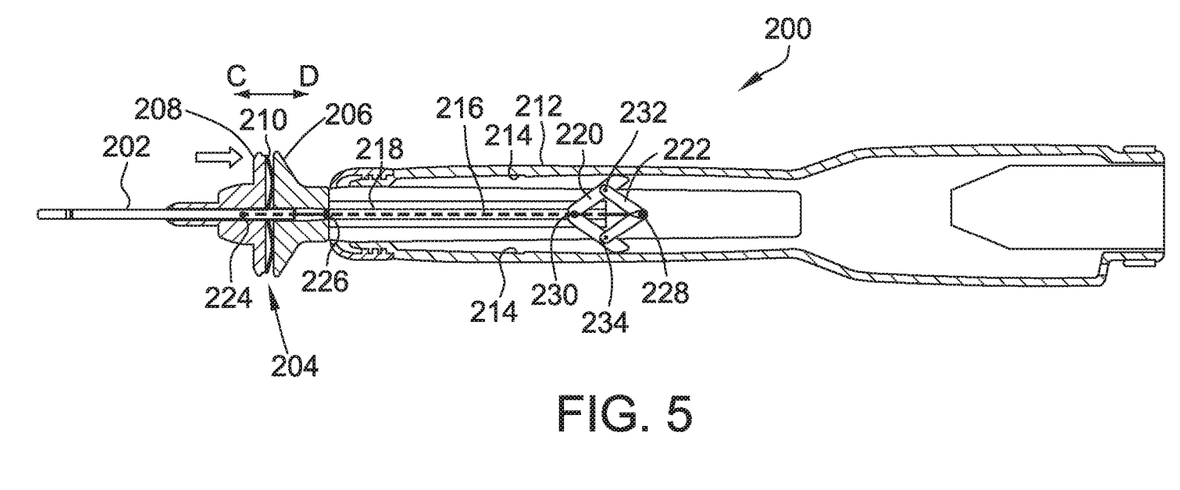
FIGS. 5 and 6 are cross-sectional views of a plunger-type catheter including one embodiment of an actuator restraining assembly of the present disclosure.
Figure 6:
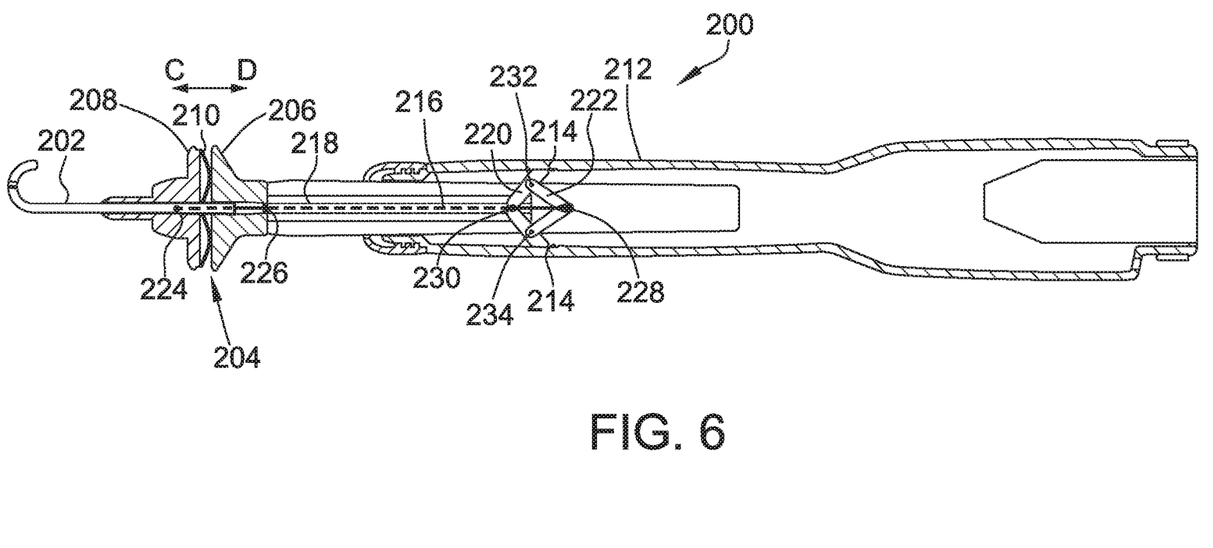

Referring now to FIGS. 5 and 6, there is illustrated the use of an actuator restraining assembly in accordance with embodiments of the present disclosure. FIGS. 5 and 6 illustrate plunger-type catheter 200 including catheter shaft 202 (FIG. 5 shows catheter shaft 202 in an un-deflected state and FIG. 6 shows catheter shaft 202 in a deflected state), split actuator mechanism 204, including proximal actuator mechanism 206, distal actuator mechanism 208, resilient member 210, handle 212, and inner wall of handle 214. Also shown in FIGS. 5 and 6 are connecting rod 216, connecting sheath 218, brake element 220 and release element 222. Although illustrated in FIGS. 5 and 6 with a single brake element 220 and a single release element 222, it is within the scope of the present disclosure for the actuator restraining assembly (and hence plunger-type catheter 200) to include 2, 3, 4, 5 or more brake elements and/or release elements. Connecting rod 216 is attached to distal actuator mechanism 208 at connecting point 224 such that as split actuator mechanism 204 is moved either proximally or distally (with respect to handle 212 or in a direction along C or D) connecting rod 216 moves in the same direction. Connecting sheath 218 is attached to proximal actuator mechanism 206 at connecting point 226 such that as split actuator mechanism 204 is moved either proximally or distally (with respect to handle 212 or in a direction along C or D) connecting sheath 218 moves in the same direction.

Release element 222 is attached to connecting rod 216 at connecting point 228 and brake element 220 is attached to connecting sheath 218 at connecting point 230. Further, release element 222 and brake element 220 are attached to each other at connecting points 232 and 234 such that they can move simultaneously upon the application of a force.

FIG. 5 illustrates plunger-type catheter 200 in an "unlocked" position; that is, FIG. 5 illustrates brake element 220 in an unlocked conformation such that while brake element 220 is in contact with inner wall of handle 214, it is not in engaged contact with inner wall of handle 214 (in this unlocked conformation there is little to no resistance between brake element 220 and inner wall of handle 214). In use, when proximal actuator mechanism 206 of plunger-type catheter 200 of FIG. 5 is moved along direction C, or distally with respect to handle 212 (i.e., out of handle 212), brake element 220 remains in contact with inner wall of handle 214 as described herein but can slide along inner wall of handle 214 with minimal effort, friction, or resistance (to allow deflection of catheter shaft 202, as described herein). Once a sufficient force is exerted on proximal actuator mechanism 206, proximal actuator mechanism 206 (and distal actuator mechanism 208) will begin to move along direction C, thus pulling connecting sheath 218 and connecting rod 216 in the same direction, such that as both proximal actuator mechanism 206 and distal actuator mechanism 208 move along direction C, so will brake element 220 and release element 222 such that catheter shaft 202 may be put into a deflected position, as illustrated in FIG. 6. Because release element 222 is attached to connecting rod 216 and brake element 220 is attached to connecting sheath 218, and because brake element 220 is in an unlocked configuration with respect to inner wall of handle 214, the actuator restraining assembly, including both brake element 220 and release element 222 can easily move within handle 212 as split actuator mechanism 204 is moved along direction C (distally with respect to handle 212).

FIG. 6 illustrates plunger-type catheter 200 in a "locked" position; that is, FIG. 6 illustrates brake element 220 in a locked or engaged conformation such that brake element 220 is in direct engaged contact (i.e., significantly increased friction or resistance due to the design of brake element 220 and inner wall of handle 214 as described herein) with inner wall of handle 214 of handle 212 such that catheter shaft 202 may remain in a deflected state. In use, once split actuator mechanism 204 of plunger-type catheter 200 of FIG. 6 has moved along direction C (distally with respect to handle 212) as described above and sufficiently deflected catheter shaft 202 and the force along direction C is removed, because of the tension created on deflected catheter shaft 202 (and the internal wires (not shown) directing catheter shaft 202) as described above, split actuator mechanism 204 naturally tends to retract in direction D (proximally with respect to handle 212), which would, in the absence of some type of restraining device result in the unwanted decreasing amount of deflection of catheter shaft 202 (i.e., return to a neutral state). That is, when the desired amount of deflection of catheter shaft 202 is reached and the operator releases pressure on split actuator mechanism 204, split actuator mechanism 204 and connecting sheath 218 naturally begin to move along line D (proximally with respect to handle 212), and brake element 220 comes into engaged contact (i.e., significantly increased friction or resistance) with inner wall of handle 214 almost immediately to create friction or locking at the interface of brake element 220 and inner wall of handle 214 to effectively "lock" split actuator mechanism 204 in place and maintain the desired amount of deflection of catheter shaft 202. Split actuator mechanism 204 will then remain in this "locked" position until a user applies a force to distal actuator mechanism 208 along line D (proximally with respect to handle 212) sufficient to overcome the spring force between distal actuator mechanism 208 and proximal actuator mechanism 206. When this occurs and distal actuator mechanism 208 and proximal actuator mechanism 206 come together and move along line D, brake element 220 is pulled slightly away from inner wall of handle 214 (due to movement of connecting rod 216 along line D which results in release element 222 "releasing" brake element 220) such that an "unlocking" occurs and catheter shaft 202 can be put back into an undeflected state.

In another embodiment of the present disclosure, the actuator restraining assembly as described herein and including a brake element, a release element, a connecting sheath, and a connecting rod, may be utilized in combination with an additional element or elements to further improve the "locking" or restraining capability of the actuator restraining assembly and/or to improve the overall control and amount of the deflection of the catheter shaft. In one specific embodiment, the actuator restraining assembly may be used in combination with a resilient friction assembly, which may include a resilient friction ring comprised of silicone as described herein, and as illustrated for example in FIGS. 3A-3C.

Other embodiments of the present disclosure include methods of using the medical devices described herein, and particularly to using a plunger-type catheter including an actuator restraining assembly as described herein. In one specific embodiment, a method of deflecting the distal region of a medical device, such as the distal region of a catheter shaft, is disclosed. In this embodiment, the method comprises first providing a medical device including a catheter shaft having a proximal region and a deflectable distal region and an active drive assembly comprising a split actuator mechanism that is configured to engage the proximal region of the catheter shaft and is at least partially movable with respect to a handle along a longitudinal axis thereof. The medical device further includes an actuator restraining assembly as described hereinabove. The actuator restraining assembly includes a brake element, a release element, a connecting sheath, and a connecting rod disposed in the handle. The connecting rod is attached to the distal actuator mechanism, and the connection sheath is attached to the proximal actuator mechanism. The brake element is attached to the connecting sheath and the release element is attached to the connecting rod. The brake element is sized and configured to contact an inner wall of the handle to thereby provide resistance to proximal movement of the connecting sheath (and hence the proximal actuator mechanism) with respect to the handle. The split actuator mechanism is distally advanced with respect to the handle to a position wherein the deflectable distal region of the catheter shaft is in a deflected configuration and the actuator mechanism is allowed to at least partially retract in a proximal direction with respect to the handle such that at least a portion of an inner wall of the handle is contacted by the brake element to create a frictional locking resistance therebetween sufficient to limit further proximal movement of the split actuator mechanism with respect to the handle. With this method, including the actuator restraining assembly, the operator does not have to overcome substantial friction when he/she desires to reduce the amount of deflection of the catheter shaft. Additionally, the overall performance and lifetime of the medical device is improved.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An actuator restraining assembly for a medical device comprising:
   a handle;
   a connecting sheath disposed in the handle and coupled to a proximal actuator mechanism;
   a connecting rod disposed at least partially in the connecting sheath and coupled to a distal actuator mechanism;
   at least one brake element attached to the connecting sheath;
   at least one release element coupled to the at least one brake element and attached to the connecting rod;
   wherein the at least one brake element is sized and configured to contact an inner wall of the handle to thereby provide resistance to proximal movement of the connecting sheath with respect to the handle.

2. The actuator restraining assembly of claim 1 wherein the at least one brake element has a length that is longer than a length of the at least one release element.

3. The actuator restraining assembly of claim 1 wherein the at least one brake element is attached to the sheath using a ring assembly.

4. The actuator restraining assembly of claim 1 wherein the at least one brake element and/or the inner wall of the handle includes one or more friction increasing elements.

5. The actuator restraining assembly of claim 4 wherein the one or more friction increasing elements is selected from the group consisting of teeth, grooves, ridges, slits, cuts, bumps, a high friction material, and combinations thereof.

6. The actuator restraining assembly of claim 4 wherein the inner wall of the handle comprises a friction increasing element.

7. The actuator restraining assembly of claim 1 further comprising a secondary resilient friction element sized and configured to provide resistance to movement of the proximal actuator mechanism in a proximal direction with respect to the handle.

8. The actuator restraining assembly of claim 7 wherein the secondary resilient friction element is a silicone friction ring.

9. The medical device of claim 1 further comprising a resilient member positioned between the distal actuator mechanism and the proximal actuator mechanism.

* * * * *